US00PP11738P2

(12) United States Plant Patent

Zary

(10) Patent No.: US PP11,738 P2
(45) Date of Patent: Jan. 9, 2001

(54) FLORIBUNDA ROSE PLANT NAMED 'JACURPLE'

(75) Inventor: Keith W. Zary, Thousand Oaks, CA (US)

(73) Assignee: Bear Creek Gardens, Inc., Medford, OR (US)

( * ) Notice: Under 35 U.S.C. 154(b), the term of this patent shall be extended for 0 days.

(21) Appl. No.: 09/066,279

(22) Filed: Apr. 24, 1998

(51) Int. Cl.[7] ..... A01H 5/00
(52) U.S. Cl. ..... Plt./143
(58) Field of Search ..... Plt./143, 141, 144, Plt./148

(56) References Cited

U.S. PATENT DOCUMENTS

P.P. 10,450 * 6/1998 Zary ..... Plt./151

* cited by examiner

*Primary Examiner*—Howard J. Locker
(74) *Attorney, Agent, or Firm*—Klarquist, Sparkman, Campbell, Leigh & Whinston, LLP

(57) ABSTRACT

Floribunda rose plant having good production of large clusters of medium sized flowers with white petals edged in red.

1 Drawing Sheet

The present invention relates to a new and distinct variety of rose plant of the floribunda class which was originated by me by crossing the variety 'INTERprince' (U.S. Plant Pat. No. 8102), with 'JACpurr' (not patented).

The primary objective of this breeding was to produce a new rose variety having the strong clustering of the female parent and its good cut flower production and vase life, combined with the large flower of the male parent. The objective was substantially achieved, along with other desirable improvements, as evidenced by the following unique combination of characteristics that are outstanding in the new variety and that distinguish it from its parents, as well as from all other varieties of which I am aware:

1. Large clusters of five to seven flowers;
2. Medium sized flowers;
3. Good cut flower production; and
4. Novel flower coloration.

'JACurple' is a greenhouse cut rose variety whose flowers may be cut and sold in clusters. Production is 140–150 stems/m$^2$ of greenhouse. Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'INTERprince', U.S. Plant Pat. No. 8102.

*Pollen parent.*—'JACpurr' (Not patented) (JACum× MORpints.)

Classification:

*Botanical.*—Rosa hybrida.

*Commercial.*—Floribunda.

FLOWER

Observations made from specimens grown in a greenhouse environment at Somis, Calif., from January 1997 to February 1998.

Blooming habit: Continuous.

Bud:

*Size.*—About 1½ inch long when the petals start to unfurl.

*Form.*—Long, pointed ovoid.

*Color.*—When sepals first divide, bud color is White Group 155B edged in Red Group 55B. When half blown, the upper sides of the petals are White Group 155B edged in Red Group 55C, and the lower sides of the petals are White Group 155B edged in Red Group 55C.

*Sepals.*—Color: Yellow Green Group 146C. Surface texture: Covered in fine hairs. There are three lightly appendaged sepals. There are two unappendaged sepals with hairy edges.

*Receptacles.*—Color: Yellow Green Group 146D. Shape: Funnel. Size: Small (about ¼×3/16"). Surface: Smooth.

*Peduncle.*—Length: Short (about 2½"). The peduncle extends from a nearly leafless stem of up to six inches before reaching main stem. Surface: Smooth. Color: Yellow Green Group 146C. Strength: Stiff, erect.

Bloom:

*Size.*—Medium. Average open diameter is about 3½ inches.

*Borne.*—Several together, in flat clusters of five to seven flowers.

*Stems.*—Long (average about 20–24"), strong.

*Form.* —When first open: High centered. Permanence: Retains its form to the end. Outer petal edges curl slightly.

*Petalage.*—Number of petals under normal conditions: 40–45.

*Color.*—The upper sides of the petals are White Group 155B edged in Red Group 55C. The reverse sides of the petals are White Group 155B edged in Red Group 55C. The major color on the upper sides is White Group 155B.

*Variegations.*—Occasional greenish streaks on the guard petals.

*Discoloration.*—At the end of the first day: No change. At the end of the third day: No change. There is no change in color to petal drop.

*Fragrance.*—Slight.

Petals:

*Texture.*—Thin.

*Shape.*—Round.

*Form.*—Tips slightly recurved.

*Arrangement.*—Imbricated. Petaloids in the center: Few, small.

*Persistence.*—Petals drop off cleanly before drying.

*Lastingness.*—On the plant: Fair (6–7 days). As a cut flower: Fair (8–9 days).

Reproductive parts:

*Anthers.*—Size: Medium. Quantity: Many. Color: Yellow. Arrangement: Regular around styles.

*Filaments.*—Color: White.

*Pollen.*—Color: Gold yellow.

*Styles.*—Color: Reddish.

*Stigmas.*—Color: Greenish white.

Plant:

*Form.*—Bush.

*Growth.*—Vigorous; upright; branching. At maturity, in the greenhouse after one year, height is 6 feet, width is 4 feet.

Foliage: Number of leaflets on normal mid-stem leaves: Five.

*Size.*—Large (7½" long×5½" wide).

*Quantity.*—Abundant.

*Color.*—New foliage: Upper and lower side: Greyed-Purple Group 183B. Old foliage: Upper side: Green Group 139A. Lower side: Green Group 139C.

Leaflets:

*Shape.*—Pointed oval.

*Texture.*—Leathery, glossy.

*Edge.*—Serrated.

*Serration.*—Single, small.

*Petiole rachis.*—Color: Green Group 139A.

*Petiole underside.*—Smooth.

*Stipules.*—Long (about ⅞"), with a very fine serration.

*Disease resistance.*—Resistant to mildew under normal growing conditions at Somis, Calif.

Wood:

*New wood.*—Color: Greyed-Purple Group 183C. Bark: Smooth.

*Old wood.*—Color: Green Group 137C. Bark: Smooth.

Prickles:

*Quantity.*—On main canes from base: Few. On laterals from main canes: Few.

*Form.*—Long (⅞"), hooked slightly downward.

*Color when young.*—Greyed-Purple Group 185A.

Small prickles:

*Quantity.*—On main stalks: None. On laterals: None.

I claim:

1. A new and distinct variety of rose plant of the floribunda class, as herein shown and described, characterized particularly by good production of large clusters of medium sized flowers with white petals edged in red.

* * * * *

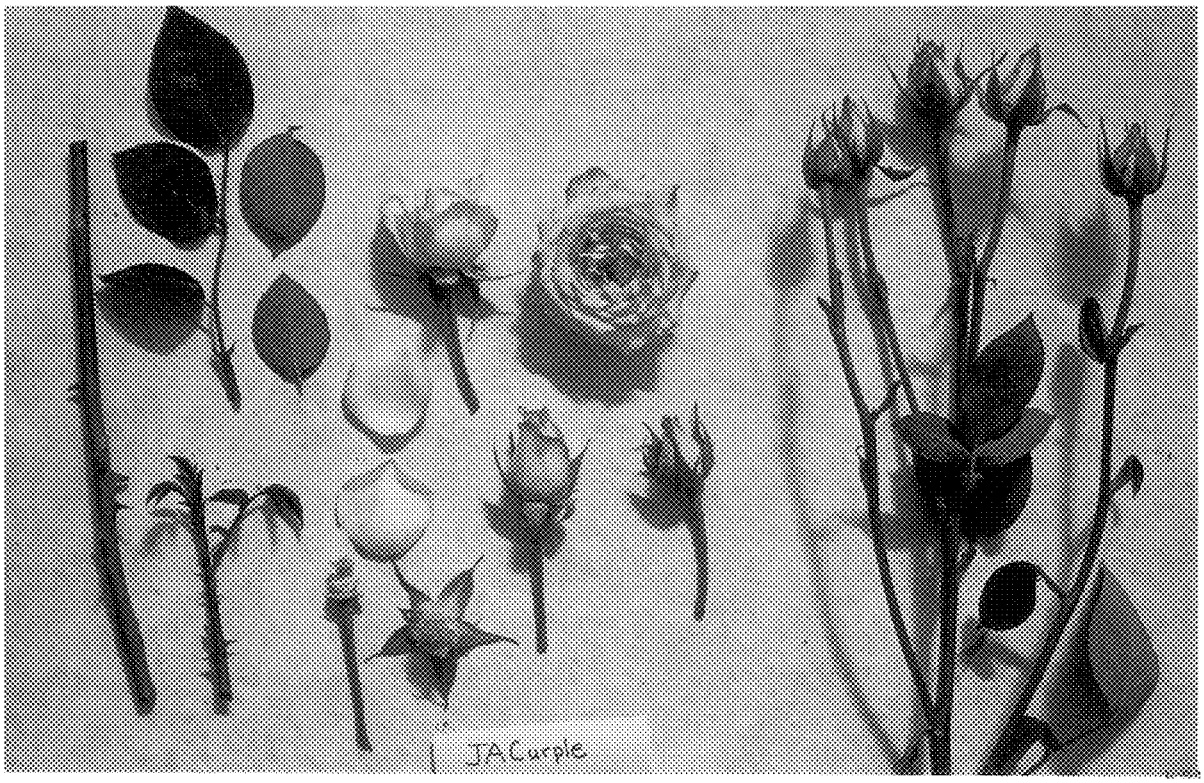
JA Curple